United States Patent [19]

Munk

[11] Patent Number: 4,475,813
[45] Date of Patent: Oct. 9, 1984

[54] DIVERGENT LIGHT OPTICAL SYSTEMS FOR LIQUID CHROMATOGRAPHY

[75] Inventor: Miner N. Munk, Riviera Beach, Fla.

[73] Assignee: Milton Roy Company, St. Petersburg, Fla.

[21] Appl. No.: 413,220

[22] Filed: Aug. 30, 1982

[51] Int. Cl.³ .................... G01N 21/59; G01N 21/64
[52] U.S. Cl. ..................................... 356/73; 356/410; 356/432; 356/417
[58] Field of Search ................ 356/409–414, 356/417, 432–437, 440, 246, 73; 250/573–576, 250/343

[56] References Cited

U.S. PATENT DOCUMENTS 4,006,990  2/1977  Munk .................................. 356/440

FOREIGN PATENT DOCUMENTS 54827  4/1982  Japan .................................. 356/319

Primary Examiner—F. L. Evans
Attorney, Agent, or Firm—Carroll F. Palmer

[57] ABSTRACT

Improved optical systems for liquid chromatographic apparatus comprise flow cells with light transparent portions through which one or more beams of light may be passed through an effluent stream flowing in the cell, one or more light sources on one side of the flow cell to project light through the cell and its contained effluent stream, one or more light limiting apertures positioned on the opposite side of the cell in the paths of the light beams, one or more positive light focusing elements positioned in the path of the light beams from the cell to the apertures to image the center of the cell at the apertures and a light sensor positioned in the path of the light beam on the side of each aperture opposite to its respective light focusing element.

Improved methods of chromatographic analysis using the new optical systems are also disclosed.

13 Claims, 5 Drawing Figures

DIVERGENT LIGHT OPTICAL SYSTEMS FOR LIQUID CHROMATOGRAPHY

BACKGROUND OF THE INVENTION

1. Field of the Invention

This invention relates broadly to liquid chromatographic apparatus and methods. More particularly, it concerns improved optical systems and methods for measuring various properties of the effluent stream of a liquid chromatographic column.

2. Description of the Prior Art

Liquid chromatography procedures are used to separate an unknown sample into its various chemical components in an elongated column packed with selective adsorbent material and to then make various types of measurements on the effluent stream from the column as to changes in certain properties of the effluent steam relative to time. Hence, in such procedures it is necessary to accurately detect and measure, on a continuous basis, the particular property under observation, e.g., refractive index, light absorbance, etc.

Ultraviolet and visible light absorption detectors are the most widely used detectors in high performance liquid chromatography and have had a significant effect on the development of such chromatography. However, improved detectors also have been developed that measure refractive index change. For example, U.S. Pat. No. 3,950,104 discusses various types of R.I. detectors and discloses and claims improved devices of one of the general types. It also describes flow and refractive index effects in small flow cells and its disclosure is incorporated herein by reference.

Most UV and visible light absorption detectors for liquid chromatography employ flat parallel transparent windows and are limited in the degree of convergence of the light illuminating the flow cell to avoid serious loss in linear dynamic range due to unequal light pathlengths through the cell. Other light absorption detectors employ a cylindrical cell with transverse illumination by more or less parallel light and also provide limited linear dynamic response range due to unequal pathlengths of light through the flow cell. The nonlinearity of response of these detectors is a consequence of the logarithmic dependence of the transmitted light on sample concentration in accordance with Beer's Law, i.e., $\log (I_o/I) = a \times b \times c$, where $I_o$ is the light incident on the flow cell, $I$ is the light transmitted through the flow cell, $a$ is the molar absorptivity, $b$ is the pathlength and $c$ is the molar sample concentration in the flow cell.

Improved detectors for chromatography have been developed for achieving a high linear dynamic response range in cylindrical cells with transverse illumination (see U.S. Pat. Nos. 3,975,104 and 4,006,990)

U.S. Pat. No. 3,975,104 describes the use of a slit aperture along the axis of the transversely illuminated flow cell to limit the light rays used in the sample concentration measurement to those which pass near the axis of the flow cell, that are therefore of nearly equal pathlength in the cell. However, the slit aperture within the cell complicates construction of the cell and perturbs the cylindrical symmetry of the flow through the cell. Slit and circular apertures have been used in a multitude of other ways in a variety of other optical systems (see for example U.S. Pat. Nos. 2,540,827; 3,075,426 and 3,999,856).

U.S. Pat. No. 4,006,990 describes the use of parallel light in conjunction with a positive lens ahead of the flow cell to focus the light near the center of the flow cell. The light rays converging near the center of the cell have nearly equal pathlengths through the flow cell. This means of obtaining nearly equal pathlengths of light in the cell requires a source of parallel light such as that obtained in expensive spectrophotometer optics or lasers.

Although there has been much research and development work on optical systems for use in liquid chromatography as indicated by the references cited above, there is a need for improved means for providing nearly equal pathlengths in transversely illuminated cylindrical flow cells in which construction of the flow cell would be simpler than in the known systems and which would provide axial symmetry of fluid flow through the cell. This invention concerns improved equipment that provides these needs while retaining all the essential advantages of the prior art.

OBJECTS

A principal object of the present invention is the provision of improved optical systems and methods for liquid chromatography.

Further objects include the provision of:

1. New means for providing nearly equal pathlengths in transversely illuminated cylindrical flow cells for liquid chromatographic apparatus.

2. Such means that do not require internal stops or apertures whereby construction of the flow cells is quite simple and axial symmetry of fluid flow through the cell is possible.

3. Such optical systems in which inherent chromatographic efficiency of the transversely illuminated cylindrical cell is maintained.

4. Such systems in which transverse temperature and refractive index gradients are oriented normal to the cell wall and do not cause significant refraction or bending of the light rays in the plane normal to the cell axis.

5. Such systems in which absence of refraction of the light rays permits direct coupling of the end of the flow cell to the end of the chromatographic column in order to maximize chromatographic efficiency where transverse temperature gradients due to frictional heating in the column would otherwise cause serious flow and refractive index sensitivity (see U.S. Pat. No. 3,950,104 supra).

6. Such optical systems that do not require a source of parallel light or focus of the incoming light near the axis of the flow cell and in which dimensions of the light source, either normal or parallel to the optic axis will be unrestricted.

7. Such systems in which stray light resulting from reflection and scattering in the optical components and housing ahead of an aperture member is largely blocked from entering a light sensor included in the system as detector means. Such stray light would otherwise reduce the upper limit of linearity of the sample concentration response of the sensor.

8. Such systems that may be directly coupled to a monochromator for adjustable wavelength selection.

9. Such systems and methods that are compatible with simultaneous multiple wavelength detection through the same plane normal to the flow axis of the flow cell so that sample constituents can be monitored at two or more wavelengths at the same time.

10. Such systems and methods that have the ability to simultaneously monitor both absorbance and fluorescence of sample constituents in similar volume elements.

Other objects and further scope of applicability of the present invention will become apparent from the detailed description given hereinafter; it should be understood, however, that the detailed description, while indicating preferred embodiments of the invention, is given by way of illustration only, since various changes and modifications within the spirit and scope of the invention will become apparent to those skilled in the art from this detailed description.

SUMMARY OF THE INVENTION

The foregoing objects are, in part, accomplished in accordance with the present invention by providing liquid chromatographic apparatus with improved optical systems for detecting changes in the chemical composition or other various properties of the effluent of a chromatographic column that comprise a flow cell having a light transparent portion through which a beam of light may be passed along an optical axis through an effluent stream flowing in the cell, a light source on one side of the cell to project light through the transparent portion and the contained effluent stream positioned in the optical axis, a light limiting aperture positioned in the optical axis on the side of the flow cell opposite to the light source, a positive focusing element positioned in the optical axis between the flow cell and the aperture to image the center of the flow cell at the aperture, and light sensor means positioned in the optical axis on the side of the aperture opposite to the focusing element. Specifically, the distance "s" from the center of the flow cell to the focusing element and the distance "s'" from the center of the lens to the plane of the aperture bears the following relationship to the focal length "f" of the focusing element:

$$1/s + 1/s' = 1/f$$

In some embodiments of the invention the focusing element is a simple biconvex lens. In other embodiments the lens is a compound convex lens or a concave mirror. The invention has particular reference to flow cells that have a substantially circular cross-section of finite radius.

The objects of the invention are further accomplished by the conducting of liquid chromatographic analysis methods, in which the effluent of a chromatographic column is streamed through a flow cell having a transparent section of substantially cylindrical cross-section, projecting non-parallel light rays from a light source along an optical axis that passes through such transparent section, positioning a light limiting aperture so that the optical axis passes through the aperture, positioning a positive light focusing element with its optical center substantially on the optical axis between the flow cell transparent section and the aperture so that the distance "s" from the center of the flow cell to the focusing element and the distance "s'" from the focusing element to the plane of the aperture bears the following relationship to the focal length f of the focusing element;

$$1/s + 1/s' = 1/f,$$

positioning a light sensor on the optical axis adjacent to the aperture on the side of the aperture opposite to the focusing element, and making measurements of light values entering the light sensor through the aperture.

In one embodiment of the new methods, the light sensor comprises an adjustable wavelength selective monochromator. In another embodiment, the measurements comprise simultaneous multiple detection of two or more wavelengths within a plurality of light beams passing respective apertures. In still another embodiment, the measurements comprise simultaneous monitoring of absorbance and fluorescence values of sample constituents of the effluent flowing in the cell.

BRIEF DESCRIPTION OF THE DRAWINGS

A more complete understanding of the invention may be had by reference to the accompanying drawings in which.

DESCRIPTION OF PREFERRED EMBODIMENTS

Figure 1:
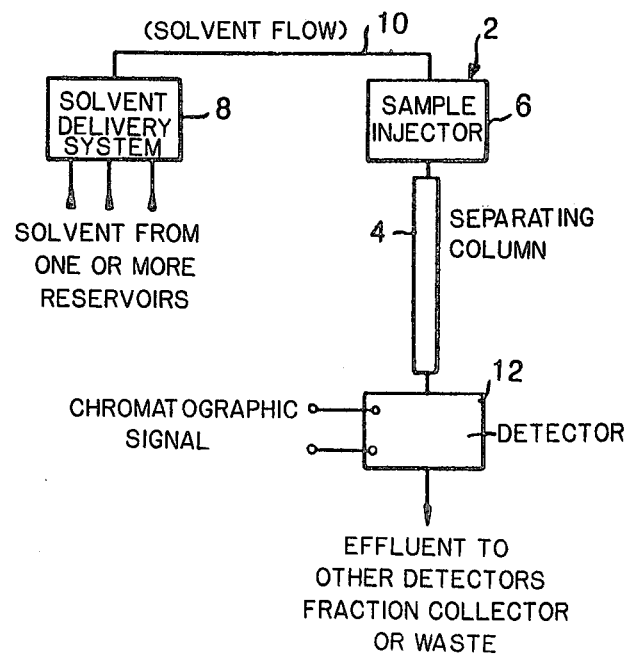
FIG. 1 is a schematic diagram of chromatographic apparatus of the invention.

Referring in detail to the drawings, the chromatographic apparatus 2 for use in accordance with the invention comprises a separating column 4, sample injector 6, solvent delivery system 8, solvent flow lines 10 and detector 12. The invention centers on improvements is the detector 12.

The detector 12 basically comprises one or more light sources 14, flow cell 16, positive light focusing element 18, limiting aperture 20 and light sensor means 22.

The light source 14 may be any of a variety of those known to the art and commercially available. The emitted light may be ultraviolet or visible or a combination of both, e.g., a broad source light which may include condensing optics. Wavelength selection for the emitted light beam may be obtained by inclusion of optical filters ahead or after the flow cell 16. Alternatively, this can be by the use of an adjustable wavelength monochromator ahead of or after the flow cell or the monochromator (not shown) may be positioned between the aperture 20 and the sensor means 22 in which the aperture serves as the entrance slit for the monochromator. In any event, an important feature of the invention is the use of a positive light focusing element 18 to image the axis of a flow cell 16, that provides effluent flow normal to the optical axis of the system, onto the plane of a limiting aperture which confines the rays used in the measurement to those which pass near the axis of the flow cell.

One of the features of the invention is that a parallel ray light source is not required so that need for expensive spectrophotometric optics or lasers are eliminated. Parallel ray light sources could be used, but the preferred embodiments of the invention use a light source that emits non-parallel rays.

The flow cells 16 that are useable with the invention are of simple design constructed for direct coupling to a chromatography column 4. They may be single beam flow cells or dual beam flow cells with a common exit for both detection and reference cells. In any event, each cell is provided with a transparent section through which a light beam from light source 14 can be passed to transit the effluent passing in the flow cell 16 from the column 4. In the preferred form, the transparent section is a short piece of cylindrical fused silica tubing having a small inside diameter (flow passage) which is clamped between suitable gaskets. By way of example, the flow cell may be of the type disclosed in my prior patent U.S. Pat. No. 4,000,990 without the inclusion of boss 46 and plate 51, the disclosure of which is incorporated herein by reference.

Figure 2:
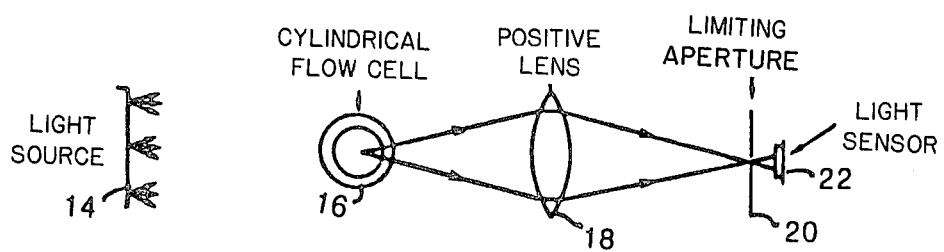
FIG. 2 is a schematic diagram of one embodiment of the optical systems of the invention.

The positive lens 18 shown in FIG. 2 is a simple biconvex lens with a focal length f. The object distance, s, of the optical system with lens 18 is the distance between the centerline of the cell 16 and the lens 18. The image distance, s', is the distance between the lens 18 and the plane of the aperture 20. Since compound lenses offer advantages over simple lenses, e.g., reduced distortion, aberration, etc., such lenses may be used to advantage in constructing the new optical systems.

The aperture may be of a fixed size or may be adjustable in size, e.g., an iris type. The aperture opening may be in the form of a circular hole. Alternatively, it may be a slit aligned parallel to the axis of the flow cell 16, or, more generally a slit aligned parallel to the image of the flow cell axis formed by the lens 18.

The nature of the light sensor means 22 in not critical and may take various form known to the art. Thus, it can be a simple photocell or more sophisticated photosensors comprising multiple electronic components. One important advantage of the new optical systems is the ability to provide to the sensor 22 a light beam that will permit simultaneous monitoring of both absorbance and fluorescence of the sample components contained in the effluent steam.

Figure 3:
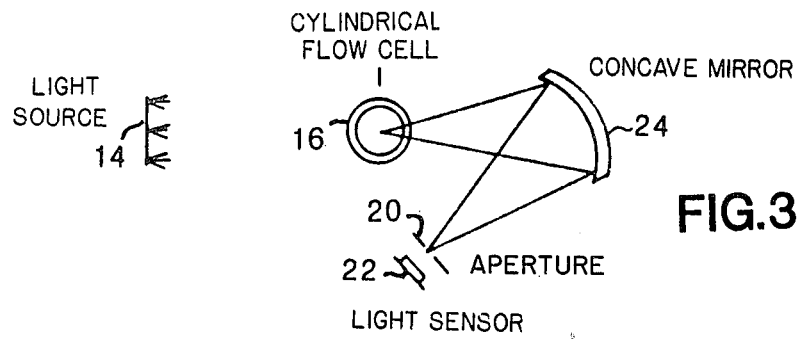
FIG. 3 is a schematic diagram of another embodiment of the invention.

FIG. 3 illustrates the embodiments of the invention in which the light focusing element is a concave mirror 24. Combinations of mirrors and lenses (not shown) are also contemplated for use in the new optical systems.

Figure 4:
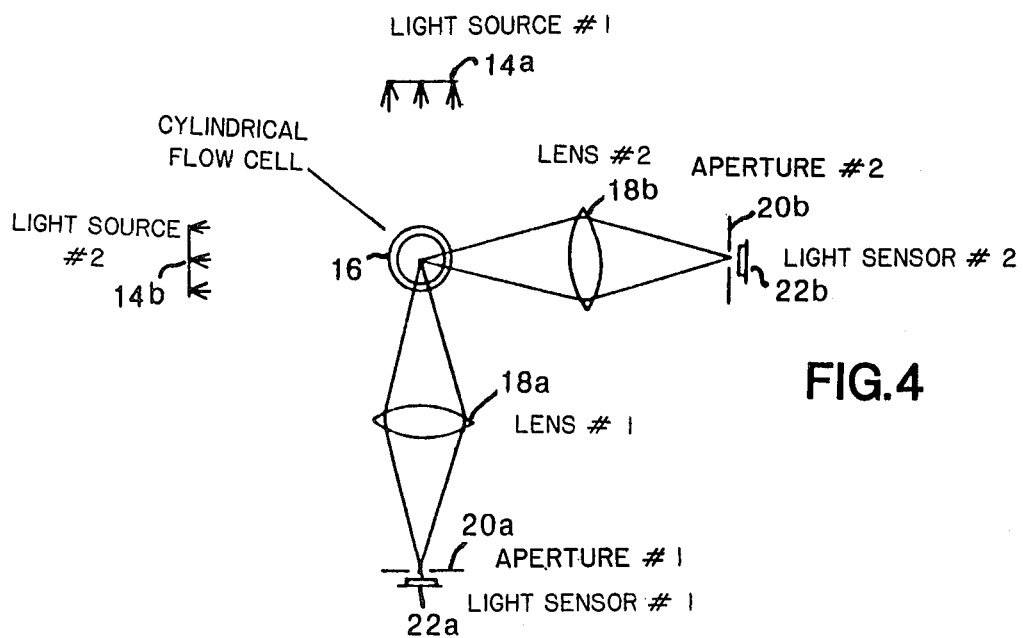
FIG. 4 is a schematic diagram of yet another embodiment of the invention.

FIG. 4 illustrates the embodiments of the invention designed for simultaneous multiple wavelength measurements. Such embodiments comprise a plurality of light sources 14a and 14b to project light on the flow cell 16, first lens 18a, aperture 20a and sensor 22a and second lens 18b, aperture 20b and sensor 22b.

Figure 5:
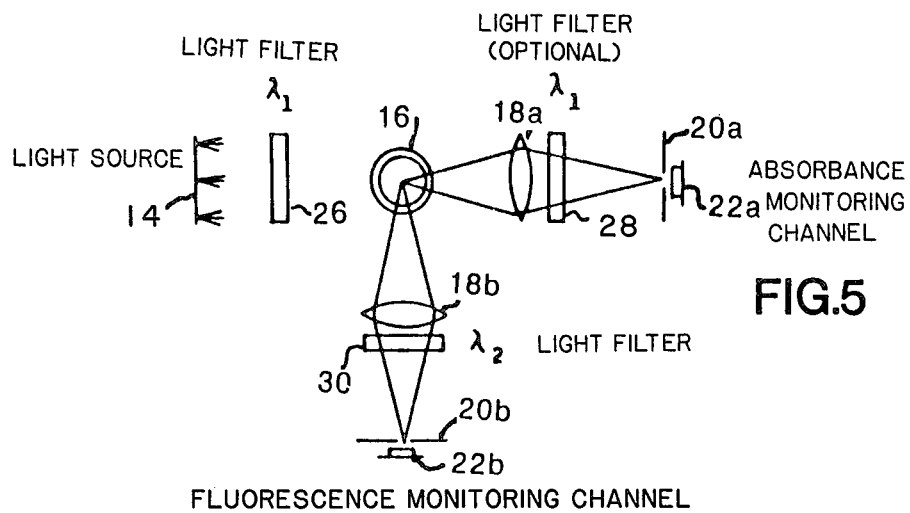
FIG. 5 is a schematic diagram of still another embodiment of the invention.

FIG. 5 illustrates the embodiments of the invention designed for combined absorbance and fluorescence measurements. Such embodiments comprise a light source 14, flow cell 16, a first lens 18a, aperture 20a and sensor 22 a and second lens 18b, aperture 20b and sensor 22b. Also included are light filters 26, 28 and 30. The filter 30, which is optional, is used to eliminate stray light from reaching the sensor 22a. The wavelength transmission of filter 28 is the same as filter 26, while that of filter 30 typically would be different.

In the embodiments of FIGS. 3–5, the arrangement and positioning of the various elements would be consistent with the arrangements as discussed relative to the embodiment of FIG. 2.

CONCLUSION

The new optical systems that provide nearly equal pathlengths in a transversely illuminated cylindrical flow cell has all the essential advantages of the prior art devices besides special advantages. An internal stop or aperture is not required in the flow cell so construction of the flow cell is simple. Also, axial symmetry of effluent flow through the cell is possible. Inherent chromatographic efficiency of the transversely illuminated cylindrical cell is maintained while transverse temperature and refractive index gradients are oriented normal to the cell wall and do not cause significant refraction or bending of the light rays in the plane normal to the cell axis. The minimized refraction of the light rays permits direct coupling of the flow cell to the end of the column in order to maximize chromatographic efficiency where transverse temperature gradients due to friction heating in the column would otherwise cause serious flow and refractive index sensitivity.

The embodiments of the invention in which an exclusive property or privilege is claimed are defined as follows:

1. In liquid chromatographic apparatus, an improved optical system for detecting changes relative to time in the chemical composition of the effluent of a chromatographic column which comprises:
   a flow cell having a light transparent portion through which a beam of light may be passed along an optical axis through an effluent stream flowing in said cell,
   a light source on one side of said cell to project light along said optical axis through said transparent portion and the contained effluent stream,
   a light limiting aperture positioned on a side of said flow cell opposed to said light source through which light emitted from said flow cell may pass,
   a positive light focusing element positioned in the path of light from said flow cell to said aperture, the distance s from the center of said flow cell to said light focusing element and the distance s' from said light focusing element to the plane of said aperture having the following relationship to the focal length f of said light focusing element:

$$1/s + 1/s' = 1/f$$

and
   light sensor means positioned on the side of said aperture opposite to said light focusing element to receive light passed through said aperture.

2. The optical system of claim 1 wherein said light focusing element is a simple biconvex lens, said light source emits non-parallel light rays and said transparent portion has a cylindrical cross-section.

3. The optical system of claim 1 wherein said light focusing element is a compound convex lens, said light source emits non-parallel light rays and said transparent portion has a cylindrical cross-section.

4. The optical system of claim 1 comprising a plurality of said combinations of aperture, light focusing element and light sensor means.

5. The optical system of claim 1 wherein said flow cell has a substantially circular cross-section of finite radius.

6. The optical system of claim 1 wherein said light sensor means is a simultaneous, multiple-wavelength light absorption detector.

7. In liquid chromatographic analysis methods, the improvement which comprises:
   streaming the effluent of a chromatographic column through a flow cell having a transparent section of substantially cylindrical cross-section,
   projecting non-parallel light rays from a light source along an optical axis that passes through said transparent section,
   positioning a light limiting aperture so that light emitted from said flow cell passes through said aperture, positioning a positive light focusing element in the path of light passing from said flow cell transparent section to said aperture so that the distance s from the center of said flow cell to said light focusing element and the distance s' from said light focusing element to the plane of said aperture bears the following relationship to the focal length f of said light focusing element:

$$1/s + 1/s' = 1/f$$

positioning a light sensor adjacent said aperture on the side of said aperture opposite to said light focusing element to receive light passing through said aperture, and making measurements of light values passing to said light sensor through said aperture.

8. The method of claim 7 wherein said light sensor comprises an adjustable wavelength selective monochromator.

9. The method of claim 7 wherein said measurements comprise simultaneous multiple detection of a plurality of wavelengths within the light beam passing said aperture.

10. The method of claim 7 wherein said measurements comprise simultaneous monitoring of absorbance and fluorescence values of sample constituents of said effluent flowing in said cell.

11. The method of claim 10 wherein said simultaneous monitoring is performed by the use of multiple light channels each passing different wavelengths of light to separate sensors.

12. In liquid chromatographic analysis methods, the improvement which comprises:

streaming the effluent of a chromatographic column through a flow cell having a transparent section of substantially cylindrical cross-section, projecting non-parallel light rays from a light source along an optical axis that passes through said transparent section, positioning a first light limiting aperture on said optical axis so that light passing along a first path from said flow cell passes through said first aperture, positioning a second light limiting aperture substantially normal to said optical axis so that light passing along a second path from said flow cell passes through said second aperture, positioning positive light focusing elements in said first and second paths of light passing from said flow cell transparent section respectively to said first and second apertures so that the distance s from the center of said flow cell to said light focusing elements and the distance s' from said light focusing elements to the plane of said apertures bears the following relationship to the focal length f of each said light focusing element:

$$1/s + 1/s' = 1/f$$

positioning a first light sensor adjacent said first aperture and a second light sensor adjacent said second aperture on the side of each aperture opposite to its respective light focusing element to receive light passing through said apertures, and making measurements of light values passing to said light sensors through said apertures.

13. The method of claim 12 wherein absorbance light values are measured by said first light sensor and fluorescence light values are measured by said second light sensor.

* * * * *